United States Patent
Quadling et al.

(10) Patent No.: US 8,487,962 B2
(45) Date of Patent: Jul. 16, 2013

(54) AUGMENTED REALITY SYSTEM FOR A DENTAL LABORATORY

(75) Inventors: Henley S. Quadling, Dallas, TX (US); Mark S. Quadling, Plano, TX (US)

(73) Assignee: D4D Technologies, LLC, Richardson, TX (US)

( * ) Notice: Subject to any disclaimer, the term of this patent is extended or adjusted under 35 U.S.C. 154(b) by 1441 days.

(21) Appl. No.: 11/682,525

(22) Filed: Mar. 6, 2007

(65) Prior Publication Data

US 2007/0211081 A1   Sep. 13, 2007

Related U.S. Application Data

(60) Provisional application No. 60/779,552, filed on Mar. 6, 2006.

(51) Int. Cl.
*G09G 5/00* (2006.01)

(52) U.S. Cl.
USPC .......................................... 345/632; 345/633

(58) Field of Classification Search
USPC ................................ 345/632, 633
See application file for complete search history.

(56) References Cited

U.S. PATENT DOCUMENTS

| | | | |
|---|---|---|---|
| 6,549,288 B1 | 4/2003 | Migdal et al. | |
| 6,646,749 B2 | 11/2003 | Bodenmiller et al. | |
| 6,664,986 B1 | 12/2003 | Kopelman et al. | |
| 6,767,208 B2 * | 7/2004 | Kaza | 433/24 |
| 2001/0002310 A1 * | 5/2001 | Chishti et al. | 433/24 |
| 2003/0068079 A1 | 4/2003 | Park | |
| 2005/0055118 A1 | 3/2005 | Nikolskiy et al. | |
| 2005/0089822 A1 | 4/2005 | Geng | |

OTHER PUBLICATIONS

Patent Cooperation Treaty, International Search Report from International Patent Application No. PCT/US07/63382, dated Sep. 5, 2008, 4 pages.

* cited by examiner

*Primary Examiner* — Jeffrey Chow
(74) *Attorney, Agent, or Firm* — David H. Judson

(57) ABSTRACT

An augmented reality system for integrating video imagery of an actual dental restoration into a computer-implemented display of a model (that represents a preparation, mesial/distal neighbors, and opposing occlusion) that has been generated from a 3D scan of a patient. The 3D scan data may be generated at a dental office remote from a location at which the augmented reality system is implemented. In one embodiment, the 3D scan data is provided to the augmented reality system as a digital impression.

14 Claims, 3 Drawing Sheets

AUGMENTED REALITY SYSTEM FOR A DENTAL LABORATORY

This application is based on and claims priority from Ser. No. 60/779,552, filed Mar. 6, 2006.

BACKGROUND OF THE INVENTION

1. Technical Field

The present invention relates generally to computer-aided manufacturing of dental items.

2. Background of the Related Art

Traditionally, a dental restoration is produced in a four step process. The first step is performed by the dentist where the area to receive the restoration is prepared using various dental tools. The second step involves taking an impression of the prepared area as well as the opposing dentition in the bite position, and sending the preparation impression to a dental laboratory (as a set of upper and lower molds), along with specifications of the kind of restoration desired. The third step occurs at the dental laboratory where two models are poured and combined into an articulator, and now accurately represent the patient's dentition in the relevant area. The articulated model (made out of some hard material) shows the prepared area and adjacent teeth, as well as the opposing teeth. The fourth step involves the manufacturing of the restoration according to the specifications provided by the dentist, and ensuring that the restoration fits on the model and does not interfere with the adjacent or opposing dentition. This is done by the laboratory technician placing the restoration in progress onto the preparation model in the articulator and making sure that there is no interference when the articulator is positioned into the closed position. In particular, the technician must check the fit at the margin, that the contacts with the neighboring teeth are correct, and that the occlusion is correct.

Recently, there have been steady advances in the use of CAD/CAM technologies in the dental laboratory. Instead of creating the restoration out of some time honored technique (such as a lost wax casting technique), the restoration may be totally or partially machined in a milling machine or created in a 3D printer. There may or may not be a process of stacking porcelain onto the created substructure. These techniques, however, typically include the step of digitizing the model, and the created restoration may still be placed on the model to check the contacts and the occlusion.

With the advent of the CAD/CAM systems in the dental office, however, a new wrinkle arises. An in-office CAD/CAM system may include a milling machine, which enables the dentist to design and mill the restoration while the patient is there, and place the restoration in a single office visit. If this process is used, however, the workflow of the dentist may be disrupted, because now substantial time needs to be allocated to design the restoration while the patient is waiting. Even with a large amount of automation, there may be some proportion of dentists who do not desire the additional complication, and would rather continue to use the dental labs. However, there is still much time and material savings to capture a digital impression instead of a real impression, and to send this data to the lab through the Internet or other means. One technique for accomplishing this is described in commonly-owned U.S. Ser. No. 11/682,194, filed Mar. 5, 2007.

Once a digital impression (namely, the digital data corresponding to a 3D scan of the preparation, the mesial/distal neighbors, and the opposing occlusion) has been received by (or otherwise received at) the dental laboratory, theoretically a technician could design and mill a full contour crown just as would have been done by the dentist in the office system. Most restorations in the lab, however, are porcelain-fused-to-metal restorations, and other types of restorations which include a stronger substructure (made of metal or zirconia or some other strong material). In these cases, the technician would design a coping or framework in the CAD software, which would then be milled in a milling machine, or created in a rapid prototyping machine. After additional processing of the coping or framework (which may include sintering), the technician would then have the option of milling out a ceramic top to place on the substructure, or layer the porcelain on top of the substructure in the traditional way. As noted above, stacking porcelain is an acquired art, and the technique produces the most aesthetically pleasing restorations. To check the contacts and the occlusion, however, a hard model (that represents the preparation, the neighbors and the opposing occlusion) typically is required.

It would be desirable to provide a technique in which the hard model would not be required. The present invention addresses this problem.

BRIEF SUMMARY OF THE INVENTION

An object of the invention is to provide a display method in which a video image of a physical dental restoration is captured and integrated into a digital impression.

A further object of the invention is to provide an augmented reality system for integrating video imagery of an actual dental restoration into a computer-implemented display of a model (that represents a preparation, mesial/distal neighbors, and opposing occlusion) that has been generated from a 3D scan of a patient. The 3D scan data may be generated at a dental office remote from a location at which the augmented reality system is implemented. In one embodiment, the 3D scan data is provided to the augmented reality system as a digital impression.

Another object of the invention is to provide a computer-implemented display method is which a video image of a physical dental restoration is captured and converted into a 3D model, with the 3D model then being integrated into a previously-generated 3D scan of a preparation and associated neighbors and occlusion. A dental laboratory technician can then use the resulting display to check a fit at a margin, that contacts with neighboring teeth are correct, and that the occlusion is correct, all without having to build a physical model of the structures corresponding to the preparation.

The foregoing has outlined some of the more pertinent features of the invention. These features should be construed to be merely illustrative. Many other beneficial results can be attained by applying the disclosed invention in a different manner or by modifying the invention as will be described.

BRIEF DESCRIPTION OF THE DRAWINGS

For a more complete understanding of the present invention and the advantages thereof, reference is now made to the following descriptions taken in conjunction with the accompanying drawings, in which.

DETAILED DESCRIPTION OF AN ILLUSTRATIVE EMBODIMENT

Figure 1:
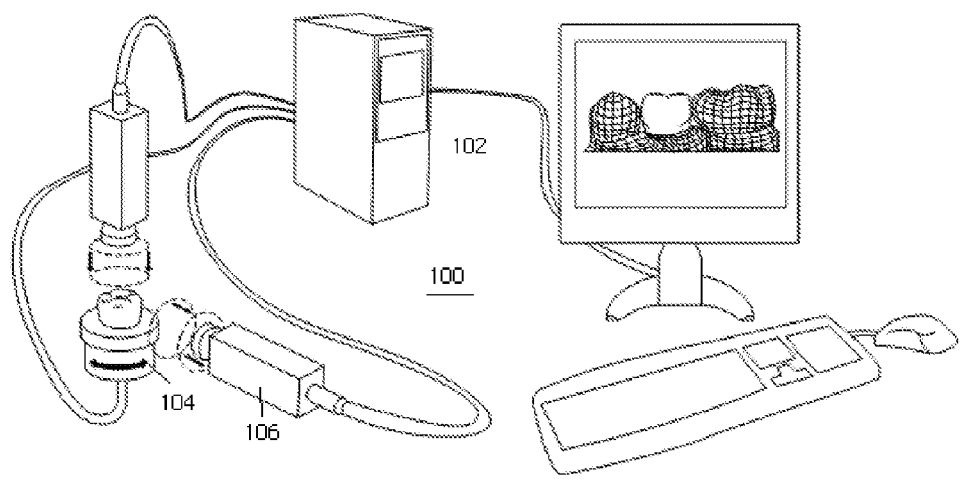
FIG. 1 illustrates a restoration mounted onto a two axis motion base, imaged by a video camera as part of an augmented reality system.
Figure 2:
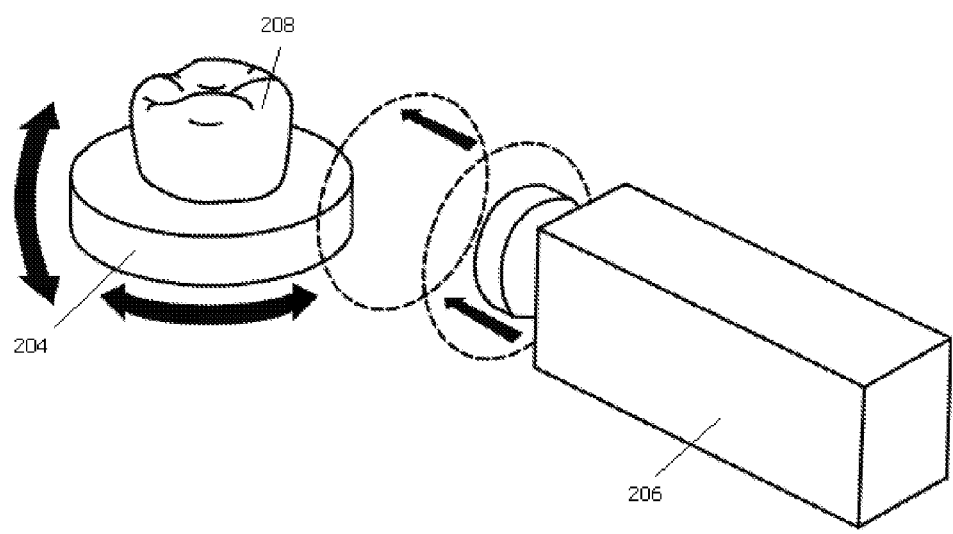
FIG. 2 illustrates the inventive augmented reality system, which displays an image (selected by the angle of the rotational base of FIG. 1) on a computer monitor along with virtual 3D data associated with a digital impression.

As illustrated in FIG. 1, an augmented reality system 100 of the present invention comprises a computer system 102, a rotational base 104, and one or more video cameras 106. The augmented reality system may be located conveniently at a dental laboratory, although this is not a requirement. One or more components of the augmented reality system may be located in different places, if desired. Although not shown in detail, one of ordinary skill in the art will appreciate that the rotational base 104 has associated mechanical elements, hydraulic elements and/or electronic elements that control the position and rotational speed of the platform. The rotational base may be under computer control. Likewise, the one or more video cameras 106 include associated optical elements, mechanical elements, and/or other control elements that control the position and operation of the device. FIG. 2 illustrates the rotational base 204 and video camera 206 in more detail. In this embodiment, the augmented reality system comprises a high quality color digital video camera, preferably with telecentric optics and magnification aimed at a single point in space. A CAM (computer-aided manufacturing) produced coping or framework 208 is temporarily mounted onto a rigid reference surface attached to a rotational base, which may rotate along two mutually orthogonal axes. Although not illustrated, a flat colored background may be placed such that the rotational base and restoration is positioned between the flat colored background and the camera, so that any background clutter is not imaged by the camera. Typically a blue or green or red background is used. Referring back to FIG. 1, the video camera 106 feeds into the computer system 102, which includes software that inputs, processes, modifies and displays the digital video data in the manner described below. The computer system also has a 3D data set, typically in the form of a "digital impression" that has been generated from a scan of a patient. As described in Ser. No. 11/682,194, filed Mar. 5, 2007, the digital impression may be created at a first location, namely, a dental office, and then transferred to a second location, e.g., a dental laboratory, at which the augmented reality system is present. The disclosure of that application is incorporated herein by reference. In one embodiment, a digital impression comprises data representing a 3D scan of a preparation, mesial-distal neighbors and occlusion (bite strip) data.

The augmented reality system (and, in particular, software executing on the computer) registers the 3D data with the images from the video system. Preferably, this is done by analyzing the video stream and comparing the stream to various projections of the digital data from different angles, along with knowledge of the current orientation of the motion base. If the optics of the camera are telecentric, then the image processing of the video stream is greatly simplified (there are no significant distortion or magnification (perspective) effects). Once the registration is complete, as long as the coping or framework is approximately rigidly attached to the rigid platform (which itself is registered with the rotational base), it is possible to align the video images with the digital data. The result of the processing is that the 3D data in the computer includes information as to the relative location and orientation of the video camera with respect to the coordinate system of the 3D data.

Figure 3:
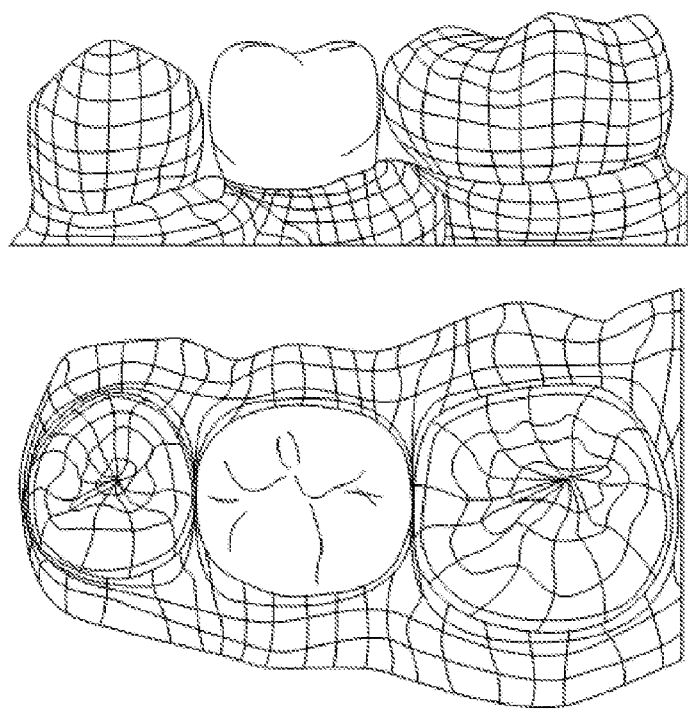
FIG. 3 illustrates a pair of augmented reality visualizations of the real video data and the virtual 3D data, from two orientations, to enable a technician to check contacts and occlusion virtually.

In the software running on the computer, the video stream from the camera is processed and augmented with the 3D data. The processing may include, for example, some modification of the image to increase contrast and sharpness of the edges. On the computer monitor, as illustrated in FIG. 3, the technician is able to see his or her work in progress, and in particular how the restoration would look from any given viewpoint (from above, from the side, or from any other vantage) if the restoration were placed on a physical model of the preparation, as long as a video image has been captured of the actual physical model from that particular orientation. Of course, by using the augmenting reality system, there is no longer any requirement to build the physical model of the preparation itself, which is highly advantageous. The display of the digital data may include additional processing and color coding to highlight areas of overlap or degree of proximity. By using this augmented display, the user is able to switch between different views to check the height of the occlusal table, or the contacts. If desired, the bite strip may also be included in the view to enable the technician to check occlusion, once again without having to build a physical model.

By obtaining a large number of camera images as a function of the angle of the rotational base (for example, 360 images for the full revolution of the bottom base, preferably for each of a number of tilt angles, and so forth), it is possible to incorporate the video imagery into the 3D scene in a relatively seamless manner. The user is able to spin the virtual 3D model around, zoom in, slice, and process and analyze the combined scene as if the video data were part of the 3D scene.

The following provides additional details on techniques that may be implemented in software to compute the 3D model of the restoration from the video signals.

To place the restoration model into the computer scene containing the preparation and the bite data, the restoration first needs to be converted into a 3D model. As is typical in computer graphics, a 3D model may be described as a collection of triangles in 3D space, which may subsequently be rendered using a technology such as OpenGL. The process outlined below may be used to generate such a model.

In particular, assume for the purposes of this explanation that 360 images have been taken (although this is not a requirement), where the platform was rotated about the vertical axis by 1 degree for each image. Assume also that the background surface is a flat green surface, so that each image appears as a restoration surrounded by green. Moreover, assume also that the virtual preparation 3D model is provided in given units, such as millimeters. To simplify the explanation, the following considers only the rotation feature of the platform, and not the tilt, although one of ordinary skill will appreciate that a similar process could also be used for cases where the tilt is also varied.

Figure 4:
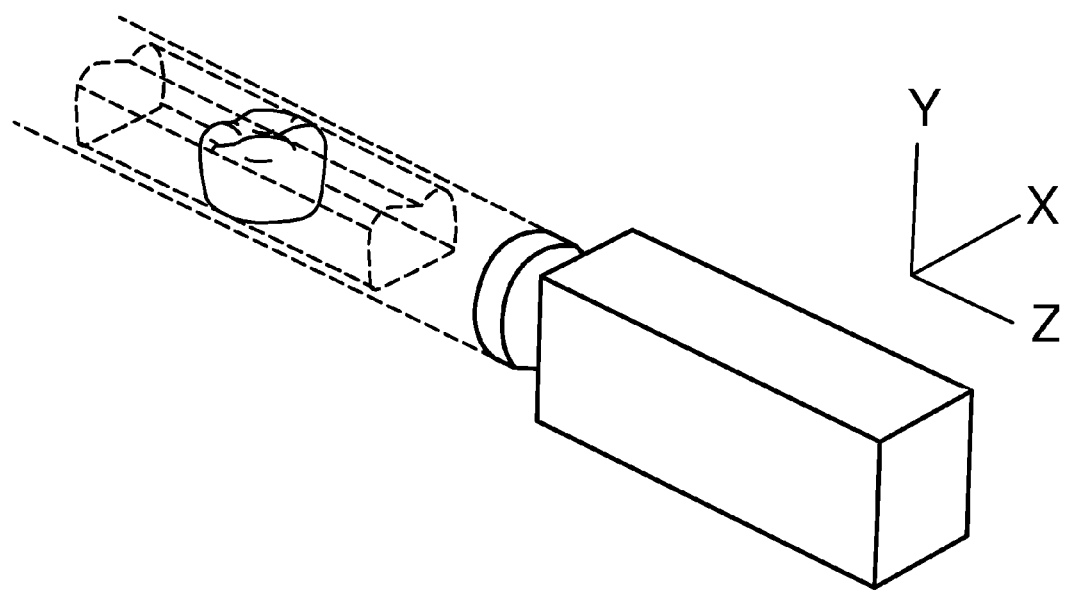
FIG. 4 illustrates how an extruded volume is computed from a silhouette.
Figure 5:
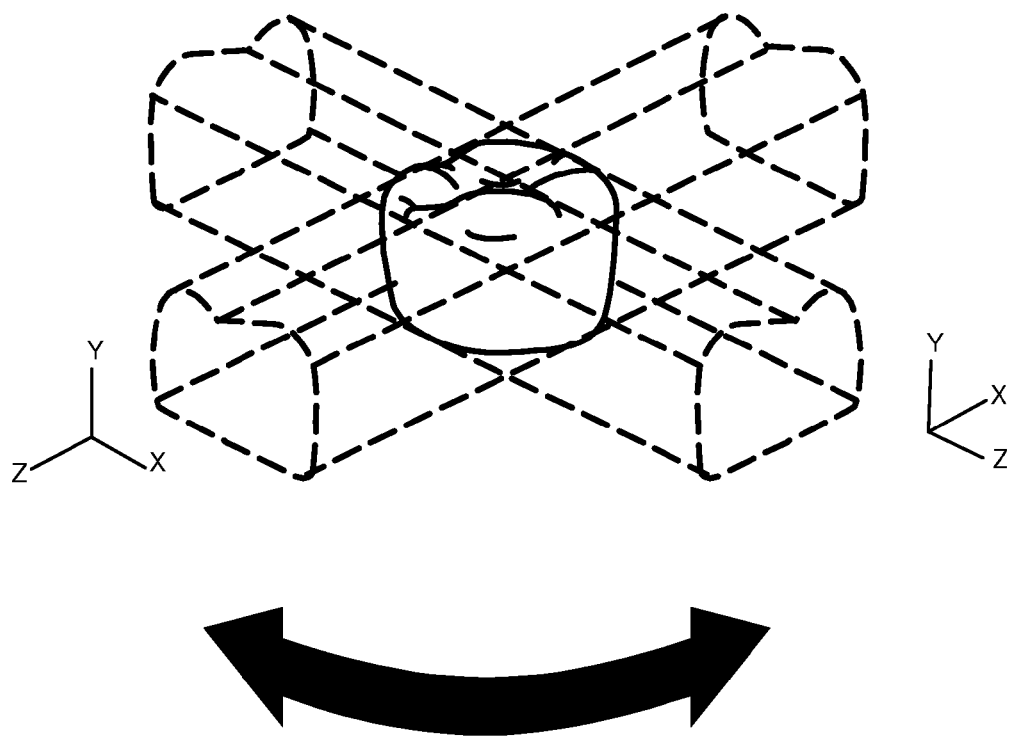
FIG. 5 illustrates how a technique for intersecting the extruded volume to form a solid representing the restoration model.

For each image $A_i$ where i goes from 0 to 360, analyze $A_i$ and find that portion of the image that does not contain green (within some tolerance). The outline of the non-green area is obtained, and this outline is then described as a 2D curve $C_i$ where the X coordinates are measured in horizontal pixels and the Y coordinates are measured in vertical pixels. The Z coordinates are set to 0. The curve $C_i$ may be converted into millimeters using known (e.g., previously calibrated) properties of the telecentric lens. For example, a simple model provides for a scaling factor to convert pixels to millimeters. This model may be calibrated by imaging a known cube in the imaging space, and measuring the size of the cube in pixels. Thus, for example, if a 10 millimeter cube is imaged, and is measured to be 100 pixels horizontally, then a horizontal scaling factor of 0.1 could be used to convert pixels to millimeters. At this point the curve $C_i$ is a 3D curve in the local coordinate system of the camera, where the X axis is along the horizontal dimension of the camera, the Y axis is along the vertical dimension of the camera, and the Z axis is along the line of sight of the camera. Once $C_i$ has been determined, it is then converted into an extruded solid $V_i$, where the axis of extrusion is along the camera axis. This process is illustrated in FIG. 4. The solid $V_i$ is then rotated around the Y axis (which is the axis of rotation of the rotation table) by the angle i degrees. This can be done in a standard manner using a 4×4 matrix. The collection of $V_i$ are intersected to form a solid model W (for example, voxel-based), which may than have its boundary extracted as a triangular mesh. FIG. 5 shows this process for two such volumes, and the full process would intersect 360 (or some given subset) of these volumes. The resulting restoration model is then rendered along with the virtual preparation (and bite strip) models, as has been previously described.

If desired, the actual images from the video camera may be used to texture map the model. For example, each triangle in W could be analyzed and have its normal computed. The image most perpendicular to that normal could then be used to texture map that triangle.

Figure 6:
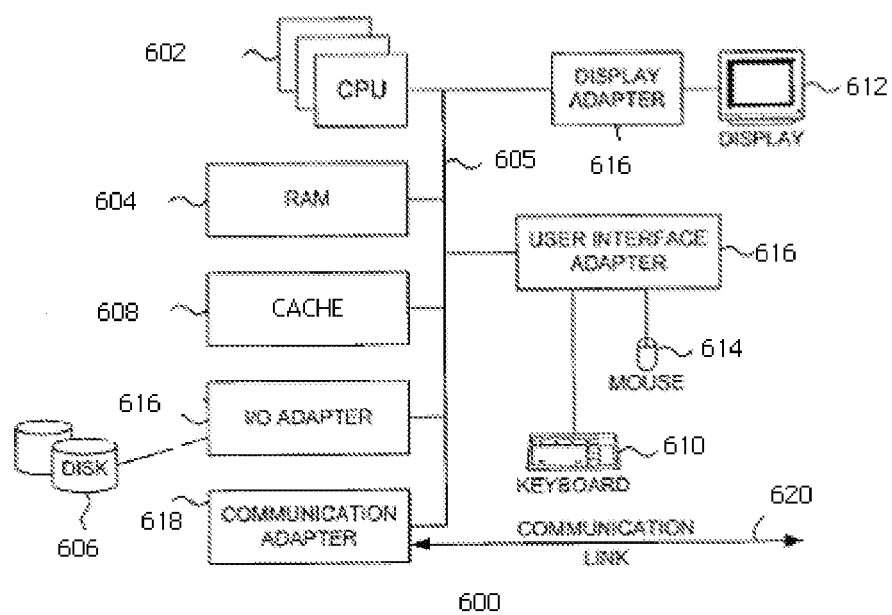
FIG. 6 is a simplified block diagram of a representative data processing system in which the invention may be implemented.

FIG. 6 illustrates a representative data processing system 600 for use in processing the video data in the above-described manner and integrating the resulting 3D restoration model into the virtual preparation model. A data processing system 600 suitable for storing and/or executing program code will include at least one processor 602 coupled directly or indirectly to memory elements through a system bus 605. The memory elements can include local memory 604 employed during actual execution of the program code, bulk storage 606, and cache memories 608 that provide temporary storage of at least some program code to reduce the number of times code must be retrieved from bulk storage during execution. Input/output or I/O devices (including but not limited to keyboards 610, displays 612, pointing devices 614, etc.) can be coupled to the system either directly or through intervening I/O controllers 616. Network adapters 618 may also be coupled to the system to enable the data processing system to become coupled to other data processing systems or devices through intervening private or public networks 620.

Although not required, the virtual preparation model may be associated with a "digital impression" that may be obtained at a first location (e.g., a dental office) using an intra-oral digitizer, such as the E4D Dentist system available from D4D Technologies, LLC and described by commonly-owned, co-pending U.S. Pat. No. 7,184,150. In particular, the prepared area and adjacent teeth are scanned using the digitizer, and a 3D model of the prepared area is obtained. The patient may also be instructed to bite on a bite strip, and the bite strip subsequently scanned to get the opposing dentition model. This information may then be used to produce a virtual preparation 3D model in the form of a data set, which is then transmitted (directly, or via an intermediate server) to a location at which the augmented reality system is executing. Such a process can be performed using the Design Center available as part of the E4D Dentist system from D4D Technologies, LP, Richardson, Tex. Of course, the present invention is not limited for use with such systems. Generalizing, all that is required is a virtual model of the scanned preparation, and optionally one or more additional scans such as an opposing side or a bite strip.

While the augmented reality system of the present invention has been described in the context of a technician visualizing how a restoration fits within a virtual 3D preparation model, this is not a limitation of the present invention. The system may be used in a dental laboratory whenever it is desired to integrate an image of a physical dental item into a virtual scene. Examples of such additional use scenarios include, without limitation, visualizing into a virtual scene such dental items as implants, abutments, bridges, orthodontic appliances, oral appliances, and other physical dental items. The virtual scene may include data from 3D scans, x-ray data, CT scan data, or some other virtual representation of an oral cavity, comprising tooth structure, soft tissues and internal structures such as bone structures.

Variants

There are many other useful variations on the augmented reality system. One such variant is the use of stereoscopic displays. In particular, in one alternative embodiment, as illustrated in FIG. 1, two video cameras are employed. Each camera is focused in essentially the same direction as each other, but a small distance apart and subtending a small angle. This configuration simulates the two "eyes" of a stereoscopic imaging system. In this embodiment, the software processes the two video streams in much the same way as described above (with respect to the single camera embodiment). The display may be a stereoscopic display. An example of such a display is one that operates at double the usual refresh rate of a CRT, LCD or Projector display. In particular, the display is set up with a transparent element that imposes a distinct polarization to each frame in a pair-wise manner, such that every neighboring frame has a different polarization, and every two frames have the same polarization. By doing so, the display displays a stream of alternating stereoscopic images (left, right, left, right, and so forth). By synchronizing and matching the polarization of the left and right eye pieces of a see-through polarizing head-mounted display or head set, it is possible to recreate a true 3D virtual scene on the display. The virtually-generated images may be created using standard stereoscopic extensions of 3D libraries, such as OpenGL extensions, and the real restoration may also be viewed in a true 3D fashion. In this way, it is possible to view the entire augmented reality scene in true 3D.

In another embodiment, a head-mounted video see-through display may be used, using either one or two video eye pieces. Such displays are manufactured by Microvision, Inc., of Washington, and others. These displays project the virtual scene directly into the line of sight of the user to enable the user to augment the real scene he or she is looking at. Such a system requires either the addition of trackable markers on the fixture holding the restoration, or the implementation of a head tracking system. There are many such tracking systems available. Such tracking systems typically use active or passive IR tracking, magnetic tracking, or systems involving the use of gyroscopic or accelerometer devices, or a combination of the above.

In another embodiment, the video stream data from one, two or even more cameras may be used to generate 3D data for inclusion into the 3D scene using photogrammetric techniques. In such techniques, features on the original physical object are matched between the frames in the video data stream(s), and this matching is used to create a correspondence between separate images that, in turn, may be used to compute the 3D structure of the scanned object using close range photogrammetric techniques. Optionally, the data between the images also may be correlated (in addition to the cross correlation between images) with feedback from the motion device that is used to move the physical object being scanned. In addition, the 2D texture information of the physical object may be texture-mapped onto the 3D model to generate a textured virtual 3D model of the scanned physical object, for inclusion in a virtual 3D environment.

While certain aspects or features of the present invention have been described in the context of a computer-based method or process, this is not a limitation of the invention. Moreover, such computer-based methods may be implemented in an apparatus or system for performing the described operations, or as an adjunct to other dental restoration equipment, devices or systems. This apparatus may be specially constructed for the required purposes, or it may comprise a general purpose computer selectively activated or reconfigured by a computer program stored in the computer. Such a computer program may be stored in a computer readable storage medium, such as, but is not limited to, any type of disk including optical disks, CD-ROMs, and magnetic-optical disks, read-only memories (ROMs), random access memories (RAMs), magnetic or optical cards, or any type of media suitable for storing electronic instructions, and each coupled to a computer system bus. The described functionality may also be implemented in firmware, in an ASIC, or in any other known or developed processor-controlled device.

While the above describes a particular order of operations performed by certain embodiments of the invention, it should be understood that such order is exemplary, as alternative embodiments may perform the operations in a different order, combine certain operations, overlap certain operations, or the like. References in the specification to a given embodiment indicate that the embodiment described may include a particular feature, structure, or characteristic, but every embodiment may not necessarily include the particular feature, structure, or characteristic. Further, while given components of the system have been described separately, one of ordinary skill will appreciate that some of the functions may be combined or shared in given systems, machines, devices, processes, instructions, program sequences, code portions, and the like.

While given components of the system have been described separately, one of ordinary skill will appreciate that some of the functions may be combined or shared in given instructions, program sequences, code portions, and the like.

Having described our invention, what we now claim is as follows.

The invention claimed:

1. A display method, implemented in a computer, comprising:
    capturing a set of one or more video images of a physical dental item, the physical dental item constructed and adapted to be received in a patient's dentition within an area that has been prepared to receive the physical dental item;
    receiving a digital impression of the area; and
    augmenting a display of the digital impression with a 3D model derived from the set of one or more video images to enable visualization of how the physical dental item integrates into the area.

2. The display method as described in claim 1 further including generating the 3D model.

3. The display method as described in claim 2 wherein the step of generating the 3D model comprises:
    for each image, generating a 2D curve, converting the 2D curve into a 3D curve with respect to a local coordinate system of a camera used to capture the image, where an X axis is along a horizontal dimension of the camera, a Y axis is along a vertical dimension of the camera, and a Z axis is along a line of sight of the camera, and converting the 3D curve into an extruded solid; and
    aggregating a set of extruded solids to form the 3D model.

4. The display method as described in claim 1 wherein the digital impression illustrates one of: a preparation, at least one neighbor tooth, and opposing occlusion in the patient's dentition.

5. An augmented reality system, comprising:
    a support component on which a dental restoration is positioned for rotation about a given first axis, the dental restoration constructed and adapted to be received in a patient's dentition within an area that has been prepared to receive the physical dental item;
    a first video camera positioned adjacent the support component to capture a set of one or more video images of the dental restoration as the support component is rotated about the given first axis; and
    a computer linked to the first video camera and including a display, the computer including software (a) to receive and process the set of one or more video images into a 3D model of the dental restoration, and (b) to display the 3D model of the dental restoration within a virtual scene, the virtual scene comprising a digital impression of an area with a patient's dentition that has been prepared to receive the dental restoration augmented with the 3D model, wherein the virtual scene enables visualization of how the dental restoration integrates into the area.

6. The system as described in claim 5 wherein the virtual scene also includes a virtual bite strip model.

7. The system as described in claim 5 wherein digital impression illustrates one of: a preparation, at least one neighbor tooth, and opposing occlusion in the patient's dentition.

8. The system as described in claim 5 wherein the support component is also adapted to tilt at a given tilt axis.

9. The system as described in claim 8 wherein at least one of the video images of the dental restoration is captured at the given tilt axis.

10. The system as described in claim 5 further including at least a second video camera positioned adjacent the support component and the first video camera to capture another set of one or more video images of the dental restoration.

11. The system as described in claim 10 wherein the computer display generates a stereoscopic display of the images produced from the first and second video cameras.

12. Apparatus, comprising:
    a processor;
    computer memory holding computer program instructions executed by the processor to cause display of a visual scene comprising:
    a digital impression of an area in a patient's dentition that has been prepared to receive a physical dental item; and
    a 3D model derived from a set of one or more images of the physical dental item;
    the digital impression of the area being augmented with the 3D model to enable visualization of how the physical dental item integrates into the area.

13. The apparatus as described in claim 12 wherein the computer program instruction are executed by the processor to receive the one or more images of the physical dental item and, in response, generating the 3D model.

14. The apparatus as described in claim 13 wherein generating the 3D model comprises:
    for each image, generating a 2D curve, converting the 2D curve into a 3D curve with respect to a local coordinate system of a camera used to capture the image, where an X axis is along a horizontal dimension of the camera, a Y axis is along a vertical dimension of the camera, and a Z axis is along a line of sight of the camera, and converting the 3D curve into an extruded solid; and aggregating a set of extruded solids to form the 3D model.

* * * * *